United States Patent [19]
Haak-Frendscho et al.

[11] Patent Number: 6,008,003
[45] Date of Patent: Dec. 28, 1999

[54] NON-INVASIVE DIAGNOSTIC METHOD FOR INTERSTITIAL CYSTITIS AND BLADDER CANCER

[75] Inventors: Mary Haak-Frendscho; Angela J. Okragly; Andrew L. Niles; Ricardo Saban, all of Madison, Wis.

[73] Assignee: Promega Corporation, Madison, Wis.

[21] Appl. No.: 08/959,263

[22] Filed: Oct. 28, 1997

[51] Int. Cl.$^6$ .................... G01N 33/574; G01N 33/53
[52] U.S. Cl. .................. 435/7.23; 435/7.1; 435/7.92; 435/7.94
[58] Field of Search ......................... 435/7.1, 7.23, 435/7.94, 7.92, 7.9

[56] References Cited

U.S. PATENT DOCUMENTS

| 5,503,986 | 4/1996 | Steers et al. | 435/7.92 |
| 5,594,116 | 1/1997 | Niles et al. | 530/413 |

*Primary Examiner*—Paula K. Hutzell
*Assistant Examiner*—Lin Sun-Hoffman
*Attorney, Agent, or Firm*—DeWitt Ross & Stevens SC

[57] ABSTRACT

Disclosed is a method of diagnosing or monitoring interstitial cystitis or bladder cancer in a mammal. The method comprises analyzing urine of the mammal for the concentration of a urine-soluble protein selected from the group consisting of neurotrophin-3, nerve growth factor, glial cell line-derived neurotrophic factor, tryptase, and combinations thereof.

25 Claims, 5 Drawing Sheets

NON-INVASIVE DIAGNOSTIC METHOD FOR INTERSTITIAL CYSTITIS AND BLADDER CANCER

FIELD OF THE INVENTION

The invention is drawn to a non-invasive method for diagnosing or monitoring interstitial cystitis and bladder cancer in mammals, including humans.

BIBLIOGRAPHY

Complete bibliographic citations to the references cited below can be found in the "Bibliography," immediately preceding the claims. Each of the references cited below is incorporated herein by reference in its entirety.

DESCRIPTION OF THE PRIOR ART

Interstitial cystitis (IC) is a chronic inflammatory bladder condition characterized by urinary frequency and urgency, burning, and suprapubic pain. IC occurs predominately in women, many who suffer for years before a correct diagnosis is made. Sant, 1993. The etiology and pathogenesis of IC are unknown. Autoimmune and immune mechanisms have been implicated based on findings of immunoglobulin and complement deposits in affected bladders and of alterations in bladder mucin. Lynes et al., 1987. Defects in the protective mucosal layer of the bladder have also been suggested as a cause of IC. See, for instance, Parsons and Mulholland, 1987; Gillespie, 1993; and Parsons, 1993. A defect in the bladder surface glycosaminoglycan layer may allow toxic substances in the urine to enter the bladder wall and establish an inflammatory response. Matilla, 1983. However, defective bladder lining is not a uniform finding in IC patients. Nickel et al., 1993. Other proposed causes of interstitial cystitis include viral and bacterial infection, vascular or lymphatic obstruction, abnormal vasomotor control, genetic or endocrinologic deficiencies, and neurogenic or allergic causes. Messing, 1991.

IC is a syndrome characterized by chronic inflammation of the bladder wall resulting in tissue damage and reduced bladder capacity. The infiltrate of inflammatory cells into the bladder wall of IC sufferers is often composed predominantly of lymphocytes, with an increased number of plasma cells as the degree of inflammation increases. Lynes, 1990. Two clinical subtypes of IC are recognized: "Classic" IC is associated with perineural infiltrate, mucosal ulceration, and marked mast cell hyperplasia in the bladder wall. Ghoniem et al., 1993; Letourneau et al., 1992. "Nonulcerative" IC is associated with a relatively unaltered bladder mucosa and a sparse inflammatory response, although the same severe symptoms are present. Many reports have described a significant increase both in mast cell number and size in the bladder wall, particularly within the detrusor muscle in both classic and non-ulcerative IC. See, for instance, Sant and Meares, 1988; Feltis et al., 1987; Aldenborg et al., 1986; Christmas and Rode, 1991; Larsen et al., 1982; and Kastrup et al., 1983. Using electron microscopy, histopathological studies have demonstrated a marked increase in the number of mast cells in the bladder walls of IC patients, most of which are degranulated. Vliagoftis et al., 1992. Similarly, results of a small separate study have indicated that mast cells are also present in the bladder washings of classic IC patients. Lundeberg et al., 1993.

One study estimates that IC afflicts about 500,000 patients in the United States, with approximately 50,000 newly confirmed cases being identified annually. Hano, 1989. Approximately 90% of IC patients are women. Ratner et al., 1992. Historically, IC has been extremely difficult to diagnose. The most frequently used diagnostic approach is by "exclusion." In effect, the IC diagnosis is made by ruling out urinary tract infections, tumors, and other bladder afflictions in patients suffering from the symptoms of suprapubic pain, frequency changes, incontinence, and increased urgency.

Current treatments for IC are not much more refined than current diagnostic methods. The presently accepted method utilizes bladder distention, which requires the administration of a general anesthesia and administration of dimethylsulfoxide or other therapeutics via bladder catheterization. The protocol is both painful and timeconsuming. Furthermore, because of the difficulty in obtaining a definitive diagnosis, significant occurrences of misdiagnosis make the conventional treatments more traumatic and less effective. It has been reported that misdiagnosis and inappropriate treatment actually aggravates the condition. *Medical World News,* 1986.

As noted above, the diagnosis of IC is made on the basis of exclusion of other bladder diseases. These means are supplemented by clinical observation and cystoscopic examination of the bladder. Despite numerous efforts at a definitive diagnostic method, IC lacks a universal objective assay for diagnosis or monitoring. Attempts have been made to employ immunohistochemical staining for Tamm-Horsfall protein (uromodulin) in bladder epithelium as a marker for IC. Stone et al., 1992. These studies showed no significant correlation between the presence of Tamm-Horsfall protein and IC. Because defects in the mucosal surface of the bladder have been implicated in IC, analysis of glycosaminoglycan uronate and macromolecular uronate concentrations also has been suggested as a possible diagnostic indicator of interstitial cystitis. However, the urine of IC patients do not consistently show low values of uronates. Hurst et al., 1993. In light of the high numbers of mast cells associated with IC, urine histamine levels have been analyzed to determine whether histamine might serve as an indicator of IC. Yun et al., 1992. Results of these studies revealed that there was no significant difference in urine histamine levels between the control group and the IC group. This indicates that a spot urine histamine test is not useful for diagnosis or monitoring of IC.

Bladder cancer is the fifth most common neoplasm and twelfth leading cause of cancer death in the United States. Males are affected three times more frequently than females. Numerous chemicals are suspected bladder cancer-forming agents. However, only cigarette smoking and occupational exposure to aromatic amines are well-established risk factors.

The most common clinical presentation of bladder cancer is hematuria. Frequently, however, the diagnosis of bladder cancer is delayed because the hematuria is either intermittent or attributed to other causes such as urinary tract infection or the use of anti-coagulants. Because hematuria is often intermittent, voided urine cytology of transitional cells is conventionally used to diagnose bladder cancer. If the urinary cytology is positive, then transitional cell cancer of the urothelium is almost certainly present. But, cytological examination of transitional cells may be negative in up to half of the patients with bladder cancer. Thus, negative cytological results do not rule out the presence of bladder cancer. See, for instance, Cohen and Johansson, 1992; and Badalament et al., 1987.

An added diagnostic complication is that because transitional cells line the urinary tract starting at the kidneys, including the ureters, the bladder, and most of the urethra, once an initial diagnosis of bladder cancer is made, the entire urinary tract must be evaluated for transitional cell cancer. The renal pelvis of the kidneys and ureters are best evaluated by intravenous pyelogram or retrograde pyelogram. Cystoscopy is also an essential, and decidedly uncomfortable, part of an unambiguous diagnosis of bladder cancer.

The inflammation associated with IC and bladder cancer (and the inflammatory response in general) is characterized by the orderly recruitment and deployment of specific subsets of immune cells to sites of invasion, foreign antigen, or tissue damage.

The inflammation observed in IC and bladder cancer is characterized both by increased numbers of mast cells and by pain. Mast cells secrete the contents of their granules in response to a variety of stimuli. Tryptase is the predominant protein contained within mast cell granules. It also is a protein exquisitely specific to mast cell granules and thus serves as a marker for mast cell degranulation.

A close association of mast cells and neurons in the peripheral nervous system (PNS) has been demonstrated in a variety of painful inflammatory disorders, including IC. See Dines and Powell, 1997. Nerve growth factor (NGF), which also is synthesized and stored by mast cells (Leon et al., 1994), can activate mast cells in an autocrine fashion causing further degranulation and proliferation. In addition, NGF has trophic and survival effects on nerve cells in the microenvironment, sometimes causing hyperalgesia and activation of sensory afferent nerve endings. See Dines and Powell, supra.

Other soluble mediators associated with the activation of sensory neurons in the periphery include neurotrophin-3 (NT-3) and glial cell line-derived neurotrophic factor (GDNF). Together with NGF, these neurotrophic factors act to promote neural survival.

NT-3 is a 27 kDa homodimer containing two 119 amino acid subunits. NT-3 has been shown to support the growth and survival of sympathetic neurons and sensory neurons in the peripheral nervous system and basal forebrain and cholinergic neurons in the central nervous system. For a review of NT-3, as well as other neurotrophins, see Maness et al., 1994. NT-3 is homologous to other known neurotrophins and is also highly conserved across species.

GDNF is a 30 kDa homodimer containing two disulfide-linked 134 amino acid chain proteins. Sequence analysis of GDNF reveals it to be a member of the transforming growth factor-$\beta$ super family. It is highly conserved across species. GDNF promotes dopamine uptake and survival of midbrain neurons and is also a survival factor for developing motor neurons, cultured dopamine neurons, purified rat embryo spinal neurons, and nodose sensory neurons. The importance of GDNF in the bladder is underscored by the finding that GDNF-null mice fail to develop kidneys and form an enteric nervous system. (See Sanchez, 1996; Pichel et al., 1996; and Moore et al., 1996.) GDNF is expressed primarily in the brain by glial cells, including astrocytes. See, for instance, Lindsay, 1995.

NGF is expressed in sympathetic and sensory-innervated peripheral tissues such as the bladder, vas deferens, heart, iris, skin, splenic capsule, sciatic nerve, and submaxillary gland. At the cellular level, NGF expression has been demonstrated in mast cells, lymphocytes, smooth muscle cells, epithelia cells, astrocytes, fibroblasts, and Schwann cells. See Maness et al., supra. Like GDNF, NGF is also highly conserved across species.

NGF exists in at least two related forms 7S NGF and 2.5S NGF. 7S NGF is a complex comprising five subunits ($\alpha_2\beta\gamma_2$). The $\alpha$ subunits, which are highly homologous to the members of the glandular kallikrein family, are believed to protect the $\beta$ subunit from enzymatic degradation. The $\beta$ subunit of 7S NGF is the bioactive portion of NGF. The $\gamma$ subunits possess arginine-specific esteropeptidase activity and may play a role in regulation of 2.5S NGF bioactivity. The 2.5S NGF is composed of two identical, noncovalently linked 118 amino acid chains in the mouse. The 2.5S form originates from the dissociation and proteolytic cleavage of the $\beta$ subunit of 7S NGF. The 2.5S NGF form is solely responsible for the biological activity of NGF. In this regard, measuring the biological activity or amount of "NGF" is synonymous with measuring the activity of 2.5S/$\beta$-subunit portion of 7S NGF.

Another proteinaceous mediator relevant to the present invention is tryptase. Upon immunologic activation, mast cells degranulate and release pre-formed mediators including histamine, proteoglycans such as heparin, and proteinases including tryptase. Tryptase itself is a tetrameric, neutral, serine protease of approximately 134 kDa. Each of the four subunits is approximately 31 to 34 kDa in size. Because tryptase is found exclusively in mast cells, it is a very specific marker for mast cell degranulation. For a complete discussion regarding mast cell heterogeneity, structure, and mediators, see Nilsson and Schwartz, 1994. Elevated tryptase levels have been associated with a diverse range of human disease states and conditions, including IC. Sant and Theoharides, 1994; Niles et al., 1995.

Methods for detecting NT-3, NG-F, GDNF, and tryptase from biological solutions have been described in the prior art. Most are enzyme-linked immunosorbent assays (ELISA's). Several ELISA's for detecting these proteinaceous compounds are available commercially. See, for instance, Niles and Haak-Frendscho, U.S. Pat. No. 5,594,116, issued Jan. 14, 1997, and assigned to the Promega Corporation, Madison, Wis., for a description of an ELISA for the detection of tryptase. Promega also markets a series of ELISA's under the trademark "Emax"-brand immunoassays for the detection of NT-3, NGF, and GDNF. See Promega Technical Bulletin Nos. 243, 226, and 221, respectively.

The ELISA format is widely utilized to assay for biologically active substances and need not be described in great detail here. By way of a brief summary, ELISA's utilize antigen-specific antibodies in concert with a specific antibody-enzyme conjugate to detect and quantify proteins and protein complexes. The basic ELISA protocol can be modified in ways well known to the art to give different types of ELISA's, such as indirect, antibody-sandwich, and double antibody-sandwich ELISA's. The basic protocol for a double antibody-sandwich ELISA is as follows: A plate is coated with antibodies (called capture antibodies) specific for the protein being assayed, in the present case, NT-3, NGF, GDNF, or tryptase. The plate is then incubated with a blocking agent, such as bovine serum albumin (BSA) to block non-specific binding of immunoglobulins to the test plate. The test solution then is incubated on the plate coated with the capture antibodies, whereby the specific protein being assayed is "captured" from the test solution by the capture antibodies. The plate then is washed, incubated with specific detect antibodies, washed again, and incubated with a species-specific antibody-enzyme conjugate. After incubation, the unbound conjugate is washed from the plate and enzyme substrate is added. The presence of the bound antibody-enzyme conjugate results in a color change proportional to the amount of analyte which can be measured and quantified.

SUMMARY OF THE INVENTION

The present invention is drawn to a method of diagnosing or monitoring interstitial cystitis (IC) or bladder cancer in a mammal. The method comprises analyzing urine of the mammal for the presence of a urine-soluble protein selected from the group consisting of neurotrophin-3 (NT-3), nerve growth factor (NGF), glial cell line-derived neurotrophic factor (GDNF), and tryptase, or combination of these urine-soluble proteins. The presence of these compounds in urine positively correlates with IC or bladder cancer, or both, in the subject being tested.

More specifically, the invention is drawn to a non-invasive method of diagnosing or monitoring interstitial cystitis or bladder cancer in a human subject. The method comprises securing a urine sample from the human subject and then determining the presence and concentration in the urine sample of NT-3, NGF, GDNF, tryptase, or any combination thereof. Presence of one or more of these proteins in the urine indicates a strong possibility that IC or bladder cancer is present in the subject tested.

The preferred embodiment of the subject invention is directed to a method of diagnosing or monitoring interstitial cystitis or bladder cancer in a human subject comprising analyzing urine from the human subject for the presence of a urine-soluble protein selected from the group consisting of neurotrophin-3, nerve growth factor, glial cell line-derived neurotrophic factor, tryptase, and combinations thereof. It is preferred that the presence of one or more of these proteins be determined using a corresponding double antibody-sandwich enzyme-linked immunosorbent assay specific for the urinesoluble protein being analyzed.

In view of the above discussion, it is a principal aim of the present invention to provide a non-invasive method for diagnosing or monitoring IC or bladder cancer which is extremely sensitive, accurate, and precise, and which does not require the use of x-rays, computed tomography, cystoscopy, biopsy, or contrast agents.

As discussed fully below, there is observed a marked increase in the average amounts of these three neurotrophic factors and tryptase in the urine of patients suffering from IC or bladder cancer. The Examples, below, show that NT-3, NGF, and GDNF (all proteins that promote neuron survival) and tryptase, a specific marker of mast cell degranulation, are all elevated in the urine of IC and bladder cancer patients as compared to healthy individuals. The mediator profile in the urine of bladder cancer patients was indistinguishable from that of IC patients with respect to these same four proteins.

A particularly outstanding advantage of the present invention is that by identifying IC and bladder cancer-specific markers found in urine which can be used singly or in conjunction, the invention provides a simple, non-invasive, inexpensive, automatable, and uniform method for evaluating patients for IC and/or bladder cancer.

Further advantages of the method are manifest: The invention can serve as an objective counterpart to the subjective self-evaluation of symptoms. The invention has predictive value to assess the progression, partial remission, or resolution of IC and bladder cancer. In other words, the method provides a tool for monitoring the condition of IC and bladder cancer patients.

The invention also provides a means for stratifying patients into subsets (e.g., classic vs. non-ulcerative IC, remitted vs. active bladder cancer, etc.). Additionally, because there is no known cause (and no known cure) for IC, early and definitive diagnosis and treatment of IC (and bladder cancer) may yield valuable information about the etiology and pathogenesis of these diseases.

Taken together, the availability of a simple method for: 1) diagnosing IC or bladder cancer; 2) stratifying patients into subsets; and 3) monitoring the progression or remission of the diseases, offers the opportunity to provide earlier, more therapeutically effective, and more cost-effective treatment to IC and bladder cancer suffers, along with a concomitant reduction in the level of unnecessary treatment to those who are not suffers of these diseases. Through the resulting overall improvement in the quality of life for those afflicted with IC or bladder cancer, along with the savings in health care costs that are realized through the elimination of unnecessary treatment, the present invention marks a distinct improvement over prior art diagnostic methods for IC and bladder cancer.

Other aims, objects, and advantages of the subject method to diagnose IC and bladder cancer will appear from a complete reading of the Detailed Description of the Invention and attached the claims.

DETAILED DESCRIPTION OF THE INVENTION

Figure 1:
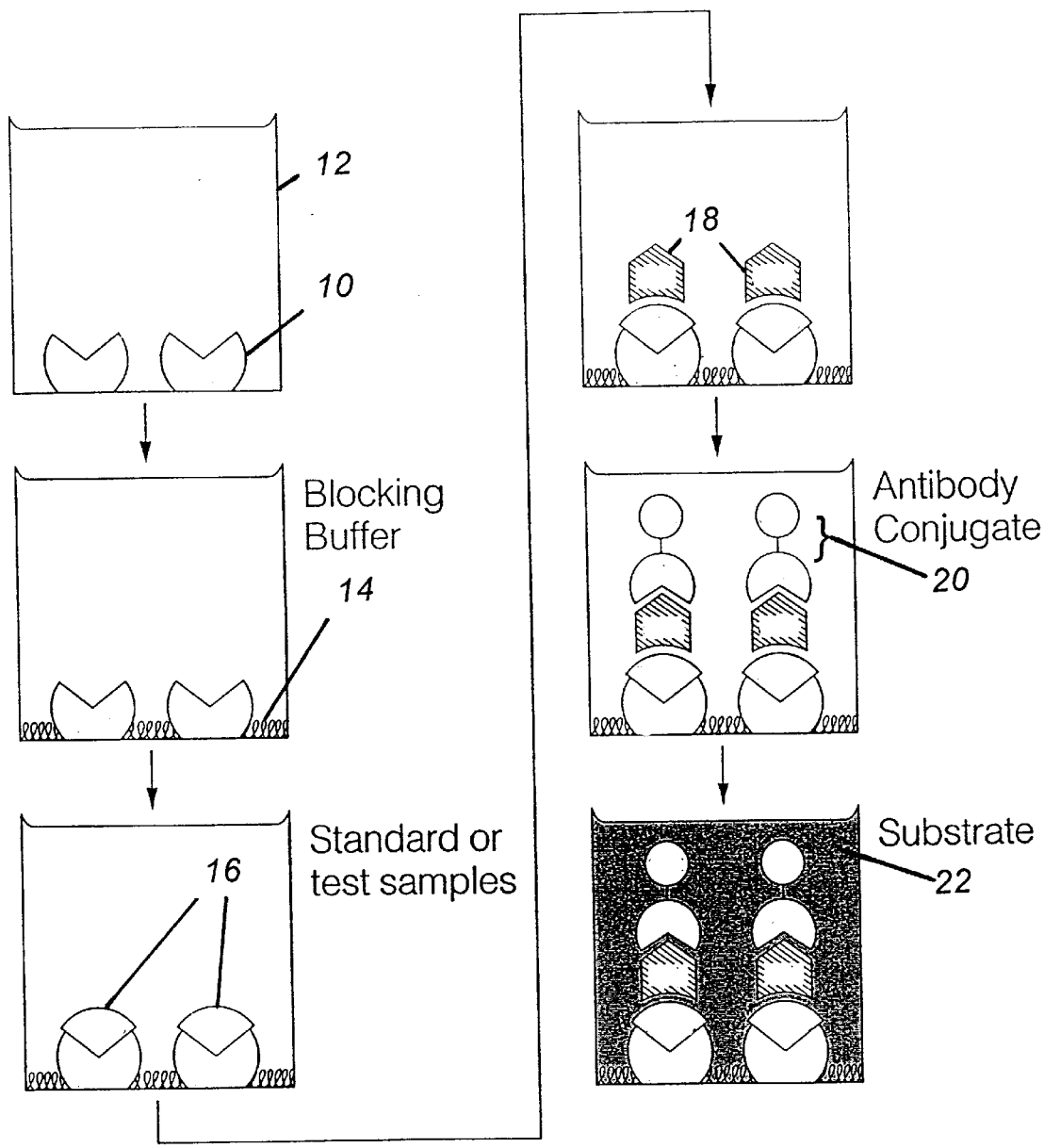
FIG. 1 is a schematic representation of a double antibody-sandwich enzyme-linked immunosorbent assay for the detection of NT-3, NGF, GDNF or tryptase.

It has been unexpectedly found that the concentration of certain neurotrophic factors and tryptase in mammalian urine bears a strong and positive correlation to the presence of both IC and bladder cancer. Consequently, by measuring the concentration of one or more of these neurotrophic factors, or tryptase, a suspected diagnosis of IC or bladder cancer can be bolstered or refuted.

The neurotrophic factors which bear a strong positive correlation to IC and bladder cancer when found in the urine are neurotrophin-3 (NT-3), nerve growth factor (NGF), and glial cell line-derived neurotrophic factor (GDNF). A fourth compound, tryptase, which is released by mast cells upon degranulation, is also found in elevated levels in the urine of subjects suffering from IC or bladder cancer.

The method of the present invention is very straightforward: urine from the subject to be tested is analyzed for the presence of one or more of the above-noted neurotrophic factors or tryptase. In the preferred embodiment of the invention, the presence and concentration of one or more of these compounds is determined by a double antibody-sandwich enzyme-linked immunosorbent assay (ELISA).

For purposes of brevity, the following description shall refer solely to detection of the neurotrophic factors and tryptase using an ELISA, which is the preferred means for detection of NT-3, NGF, GDNF, and tryptase. This, however, is for brevity only. The urine samples may be tested for the presence and concentration of NT-3, NGF, GDNF, and tryptase using any means now known to the art or developed in the future for detecting proteinaceous analytes. Such means for detection include, but are not limited to, spectroscopic and spectrophotometric means for determining the presence and concentration of NT-3, NGF, GDNF, and tryptase, including UV, visible, IR, Raman, fluorescent polarization, and/or NMR spectral means for detecting the compounds; chromatographic means for detecting the presence and measuring the concentration of the compounds, including adsorption, affinity, chelation, gel permeation, and/or ion-exchange chromatography; or mass spectrometry means for determining the presence and concentration of the compounds. The means for determining the presence of NT-3, NGF, GDNF, and tryptase in the urine is not critical to the function of the invention so long as the means chosen provide an accurate and precise measurement of the levels of NT-3, NGF, GDNF, and tryptase in the urine.

Urine Collection and Preparation

Urine samples to be tested may be collected well in advance of testing and frozen prior to treatment. If the urine sample is to be frozen prior to analysis, it is preferred that the sample be collected and placed on ice. It is much preferred that within a time period of about 2 hours, the iced sample is centrifuged to pellet cellular debris, then filtered, and the filtrate then promptly frozen at $\leq -20°$ C. Just prior to analysis, frozen samples should be rapidly thawed in a $37°$ C. water bath.

Fresh urine samples may also be used immediately after collection, centrifugation, and filtration.

Urine samples which are to be analyzed for the presence of the neurotrophic factors (NT-3, NGF, or GDNF) are preferably treated with acid immediately prior to analysis as described in Okragly and Haak-Frendscho, 1997.

The urine sample to be tested is treated with 1N HCl until its pH reaches about $\leq 3.0$. This can be confirmed by spotting an aliquot of the sample onto litmus paper. The sample then is incubated at room temperature for about 15 minutes and then neutralized by adding 1N NaOH to about pH 7.6. The sample is then analyzed as described below.

The urine samples are assayed at the highest concentration of urine that does not interfere with each ELISA. This concentration is pre-determined empirically by using the individual ELISA's for NT-3, NGF, GDNF, and tryptase to analyze serial dilutions of normal, heat-treated urine spiked with known concentrations of NT-3, NGF, GDNF, and tryptase. (NT-3, NGF, and GDNF are all available commercially from the Promega Corporation. See Promega Technical Bulletin Nos. 540, 149, and 543, respectively. Recombinant human tryptase is also available from Promega.) This same process is used to generate a standard curve for each of the ELISA's: serial dilutions of heat-treated urine spiked with purified natural or recombinant analyte are analyzed by each ELISA; corresponding standard curves for each protein are then generated according to the calorimetric results yielded by the serial dilutions.

The conventional 96-well microtiter format is ideal for use in the present invention. This format is widely used and easily automatable. There are also several commercially available spectrometers ("plate readers") for calorimetrically analyzing 96-well plates.

Enzyme-Linked Immunosorbent Assays (ELISA's)

In the preferred embodiment of the invention, the concentration of NT-3, NGF, GDNF, and tryptase in a urine sample is determined by use of a corresponding double-antibody sandwich enzyme-linked immunosorbent assay (ELISA) for each protein. The preferred ELISA format for each protein is the same:

Referring now to FIG. 1, starting at the top left and following the arrows, capture antibody specific for NT-3, NGF, GDNF, or tryptase (10) is adsorbed onto plastic microtiter plates (12). The plates are blocked with bovine serum albumin solution (14) to reduce non-specific binding. This is followed by incubation of the urine test solution containing into wells of the coated plate, allowing the capture antibody (10) to capture the analyte (16) out of the solution. The analyte is detected by incubation with a second antibody, known as a detect antibody (18). An antibody conjugate (20) is then added to the wells and binds to the detect antibody (18). In the final step, a chromogenic substrate specific for the enzyme (22) is added to each well to develop a colorimetric reaction which is read using a plate reader set to the appropriate wavelength.

Addressing each step more specifically, and again referring to FIG. 1, suitable microtiter plates are coated with capture antibodies (10) specific for either NT-3, NGF, GDNF, or tryptase. This is done by coating the microtiter plates with a capture antibody solution and incubating for 12 to 20 hours at $4°$ C. The coated plates are then thoroughly rinsed with a solution of tris-buffered saline with "TWEEN™ 20" (TBST). Non-specific residual binding to the microtiter plate itself is then blocked by incubating the plate with a blocking buffer (14). A commonly used blocking buffer is a solution of 0.05% "TWEEN™ 20" containing bovine serum albumin (BSA). The plates are again rinsed with TBST.

The urine solutions to be tested are then diluted in the blocking buffer. Preparing a number of serial dilutions is recommended. The plates are then coated with the test solutions and incubated for at least 2 hours at room temperature.

After incubation the plates are again rinsed with TBST. Other buffered solutions, such as phosphate-buffered saline or phosphate-buffered saline with "TWEEN™", also may be used.

At this point in the process, the plate appears schematically as shown in the lower left-hand panel of FIG. 1. The analyte being assayed (16) (NT-3, NGF, GDNF, or tryptase) has been captured from the urine solution by the capture antibodies (10) which are fixed to the bottom of the microtiter plate (12).

The next step is to introduce a detect antibody solution which will bind to the captured analyte. Either polyclonal antibody or monoclonal antibody can be used as the detect antibody (18). A solution of the detect antibody is prepared and the wells are coated and incubated for at least 2 hours at room temperature or from 16 to 20 hours at $4°$ C. After incubation, the plates are again washed with TBST.

The plates are then incubated with an antibody/horseradish peroxidase conjugate (20). Such antibody/horseradish peroxidase conjugates are well known in the art. A conventional method to prepare such conjugates includes using sodium periodate to oxidize the carbohydrate side chains of horseradish peroxidase, followed by the formation of a Schiff base between the activated peroxidase and amino groups of the antibody. The preferred antibodies for the conjugate are species-specific anti-IgG antibodies. The Schiff base then is reduced (sodium borohydride) to yield a stable antibody/enzyme conjugate. The wells of the microtiter plates then are incubated for at least 2 hours at room temperature. It is important here that the conjugate antibodies must not react with the capture antibody or the analyte itself.

The plates are then rinsed with TBST 3 times.

A horseradish peroxidase substrate solution (22) is then added to each well and the wells incubated for no longer than one (1) hour at room temperature. The wells then are examined spectrophotometrically at 450 nm. For colorimetric detection, horseradish peroxidase-conjugated anti-human antibody used in conjunction with the substrate 3,3',5,5'-tetramethyl benzidine (TMB) is preferred. Other colorimetric substrates, such as o-phenylenediamine dihydrochloride (OPD) and anti-mouse alkaline phosphatase conjugates function with equal success.

ELISA's for NT-3, NGF, and GDNF

Commercial double antibody-sandwich ELISA's for the detection of NT-3, NGF, and GDNF, are marketed as "Emax"-brand ImmunoAssay Systems from the Promega Corporation, Madison, Wis. (Catalog Nos. G3370, G3560, and G3240, respectively). See Promega Technical Bulletin Nos. 243, 226, and 221, respectively. All three of these ELISA's are double antibody-sandwich ELISA's as depicted in FIG. 1. Promega's ELISA for NT-3 has a linear range of from approximately 4.7 to 300 pg/ml. Promega's ELISA for NGF has a linear range of from about 7.8 to about 500 pg/ml. Promega's ELISA for GDNF has a linear range of from about 16 to about 1,000 pg/ml.

These three ELISA's all function in the same fashion as depicted in FIG. 1. In standard ELISA format, flat-bottom 96-well plates are coated with anti-human NT-3, NGF, or GDNF capture antibody (10) that binds the corresponding soluble analyte (16) from solution. Unbound analyte is removed by washing the plate. Captured analyte is then bound by a detect antibody (18), i.e., anti-NT-3 detect antibody, anti-NGF detect antibody, or anti-GDNF detect antibody. After washing, the anti-species IgG/horseradish peroxidase conjugate (20) is added to the plate and binds the sandwich complex. Lastly, a chromogenic substrate (22) such as TMB is added to the wells. The amount of bound analyte is detected by a horseradish peroxidase-catalyzed color development of TMB. The amount of analyte is proportional to the color generated in the coupled oxidation-reduction reaction. As in all ELISA's, the amount of analyte is the test well is quantitated against a standard curve generated with known amounts of analyte.

The preferred ELISA to detect tryptase for use in the present invention is described in U.S. Pat. No. 5,594,116, issued Jan. 14, 1997, and assigned to the Promega Corporation. The teaching of this patent is incorporated herein by reference in its entirety. This ELISA is also of the double antibody-sandwich variety and functions in the same fashion as described above.

EXAMPLES

The following Examples are included solely to provide a more complete understanding of the invention. The Examples do not limit the invention described and claimed herein in any fashion.

For each of the following Examples, the same three human patient populations were used. The "Control" population consisted of 7 subjects with no history of bladder disease. The "IC" population consisted of 5 patients actively suffering from interstitial cystitis. The "Cancer" population consisted of 9 patients actively suffering bladder cancer. All applicable state and federal statutes, regulations, rules, and guidelines regarding human testing were followed.

Example 1

Analyzing Urine for NT-3

Urine samples were collected from each patient, then centrifuged, filtered, divided into 1 mL aliquots, and frozen as described above. Immediately prior to ELISA analysis, an aliquot of each sample was quickly thawed in a 37° C. water bath.

A urine aliquot from each patient was acidified and neutralized as described hereinabove. An NT-3 standard curve was established and each urine sample then tested for the presence of NT-3 using the "Emax"-brand NT-3 ImmunoAssay System ELISA from Promega Corporation, following the manufacturer's instructions. (See Promega Technical Bulletin No. 243.)

A series of wells of a 96-well microtiter plate were coated with 100 µL each of a solution containing 20 µL anti-human NT-3 detect antibody diluted in 10 mL of carbonate coating buffer and incubated overnight at 4° C.

Non-specific binding was then blocked by adding to each well 200 µL of the "Block & Sample" solution provided in the "Emax"-brand ELISA. The plate was then incubated for 1 hour at room temperature without shaking.

A serial dilution (1:2) of the NT-3 standard provided in the kit, diluted in the "Block & Sample" solution, was then added to the wells (100 µL per well) and the plate incubated six (6) hours at room temperature. The plate was then washed 5 times. Anti-NT-3 detect antibody was added and the plate incubated overnight at 4° C.

Following a wash step as described above, anti-mouse IgG/horseradish peroxidase conjugate solution was then added to each well (100 µL per well) and the plate incubated at room temperature, with shaking, for 2.5 hours.

TMB substrate was then added to each well (100 µL) and the plate incubated with shaking for 10 minutes at room temperature. The reactions were then stopped by adding 100 µL per well of 1M phosphoric acid. Absorbance at 450 nm was then recorded.

Each urine test sample was analyzed in the same fashion as the standard curve. Serial dilutions of each urine sample were analyzed to empirically determine the optimum concentration of urine for ELISA analysis.

Figure 2:
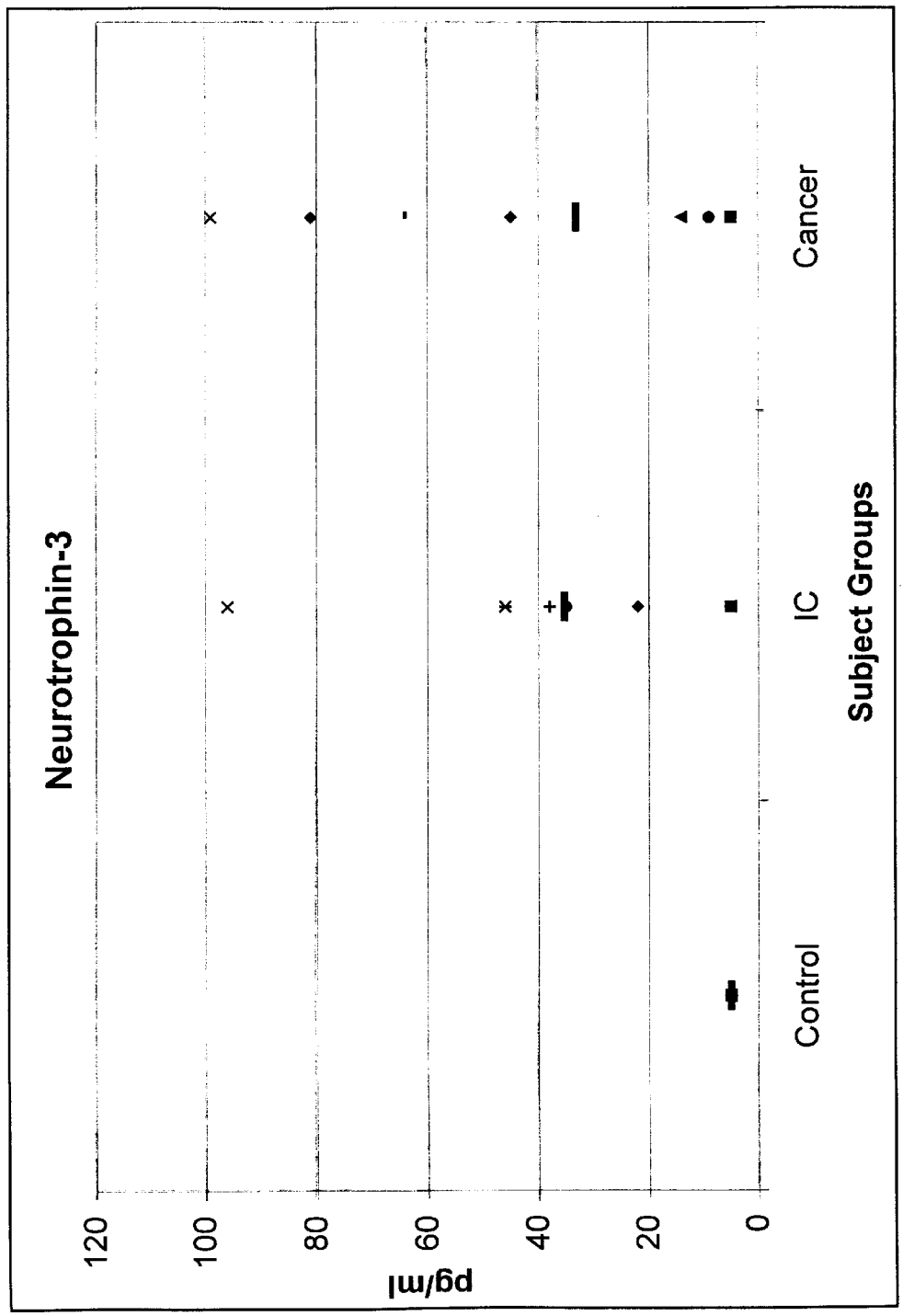
FIG. 2 is a graph depicting the concentration of NT-3in the urine of a normal human control population, a population of human IC patients, and a population of human bladder cancer patients. (See Example 1.)

The test results are depicted in FIG. 2. Each patient within the individual control, IC, and bladder cancer groups is designated by a different symbol on the graph. Symbols have been duplicated in more than one patient groups; these duplicated symbols are unrelated.

As can be seen in FIG. 2, the individuals in the IC and Cancer patient groups had markedly elevated levels of NT-3 in their urine as compared to the healthy Control patient group.

Example 2

Analyzing Urine for NGF

This Example proceeded in exactly the same fashion as Example 1 with the exception that each urine sample was tested for the presence of NGF using the "Emax"-brand NGF ImmunoAssay System ELISA from Promega Corporation, following the manufacturer's instructions. (See Promega Technical Bulletin No. 226.)

Figure 3:
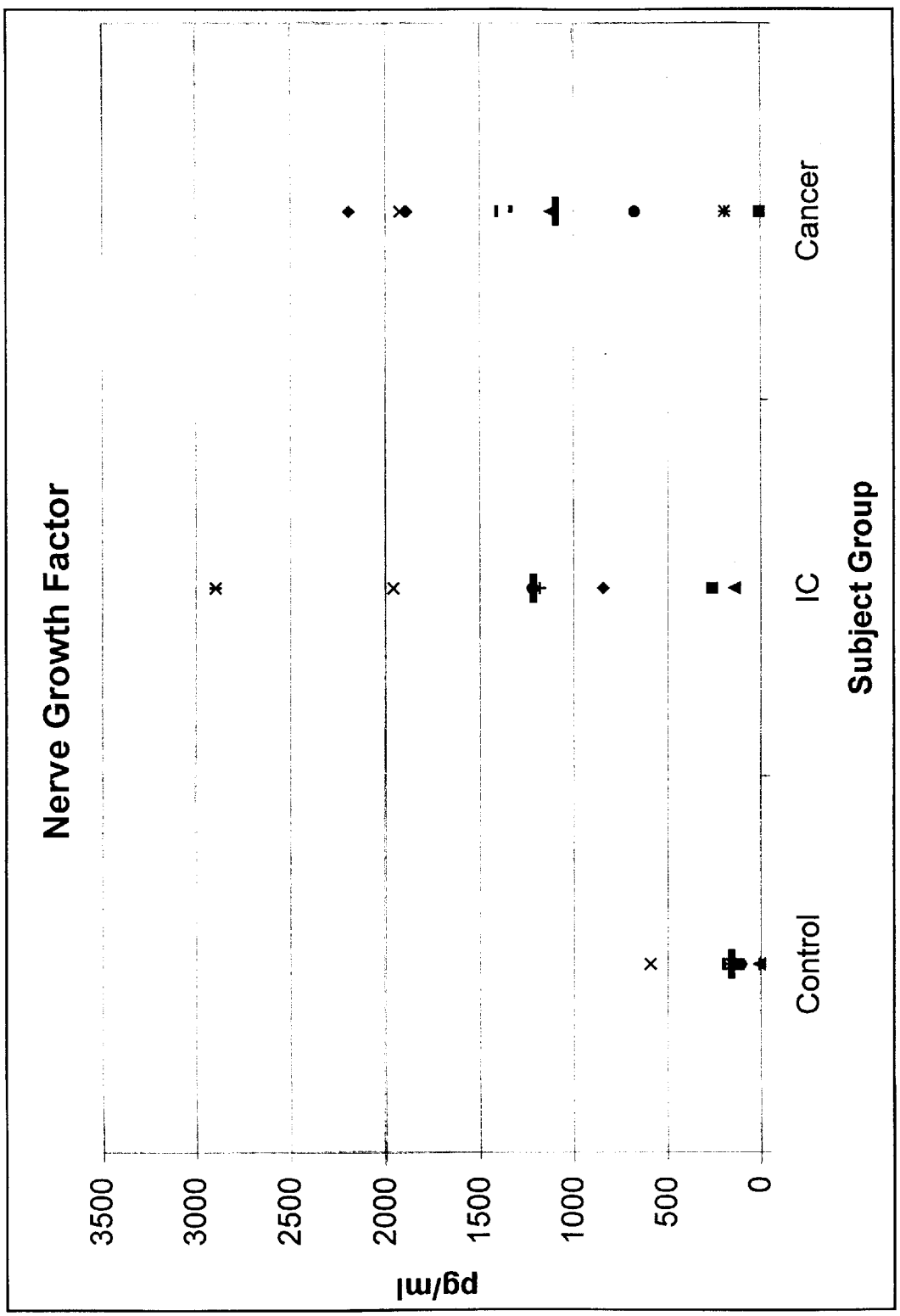
FIG. 3 is a graph depicting the concentration of NGF in the urine of the same normal human control population, the population of human IC patients, and the population of human bladder cancer patients as depicted in FIG. 2. (See Example 2.)

The test results are depicted in FIG. 3. Each patient within the individual control, IC, and bladder cancer groups is designated by a different symbol on the graph. Symbols have been duplicated in more than one patient groups; these duplicated symbols are unrelated.

In the same fashion as Example 1, here, the IC and Cancer patient groups displayed elevated levels of NGF in their urine as compared to the Control patient group.

Example 3
Analyzing Urine for GDNF

This Example proceeded in exactly the same fashion as Example 1 with the exception that each urine sample was tested for the presence of GDNF using the "Emax"-brand GDNF ImmunoAssay System ELISA from Promega Corporation, following the manufacturer's instructions. (See Promega Technical Bulletin No. 221.)

Figure 4:
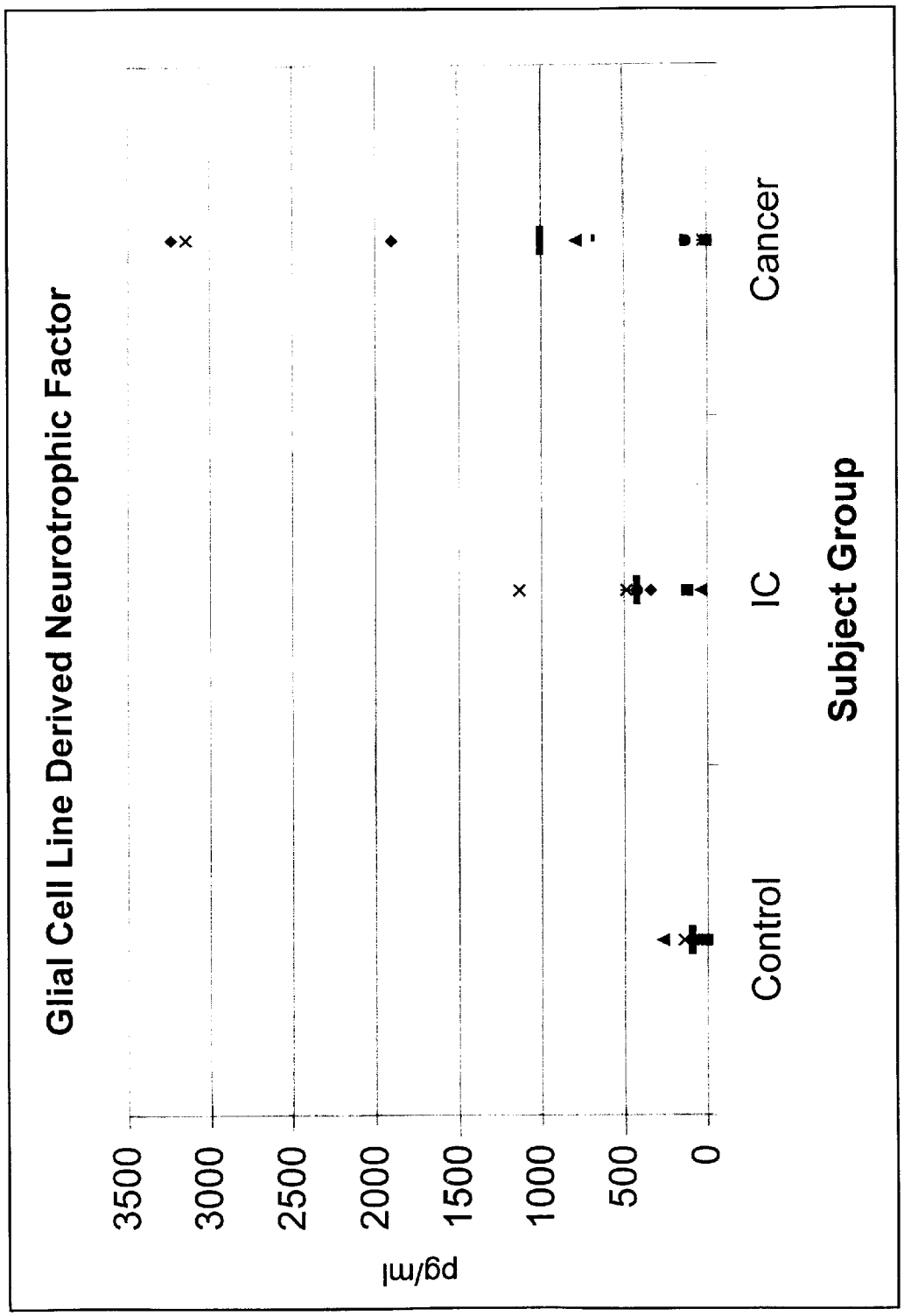
FIG. 4 is a graph depicting the concentration of GDNF in the urine of the same normal human control population, the population of human IC patients, and the population of human bladder cancer patients as depicted in FIG. 2. (See Example 3.)

The results are depicted in FIG. 4. Each patient within the individual control, IC, and bladder cancer groups is designated by a different symbol on the graph. Symbols have been duplicated in more than one patient groups; these duplicated symbols are unrelated.

In the same fashion as Examples 1 and 2, the IC and Cancer patient groups displayed elevated levels of GDNF in their urine as compared to the Control patient group.

Example 4
Analyzing Urine for Tryptase

In this Example, the double antibody-sandwich ELISA described in U.S. Pat. No. 5,594,116 was used. This ELISA uses capture antibodies which are avian-derived polyclonal tryptase-specific antibodies capable of capturing tryptase from solution and detect antibodies are monoclonal, murine-derived anti-tryptase antibodies. The same protocol described in the previous Examples was used to establish the standard curve and to analyze the test samples with the exception that the urine samples were not acid treated.

Figure 5:
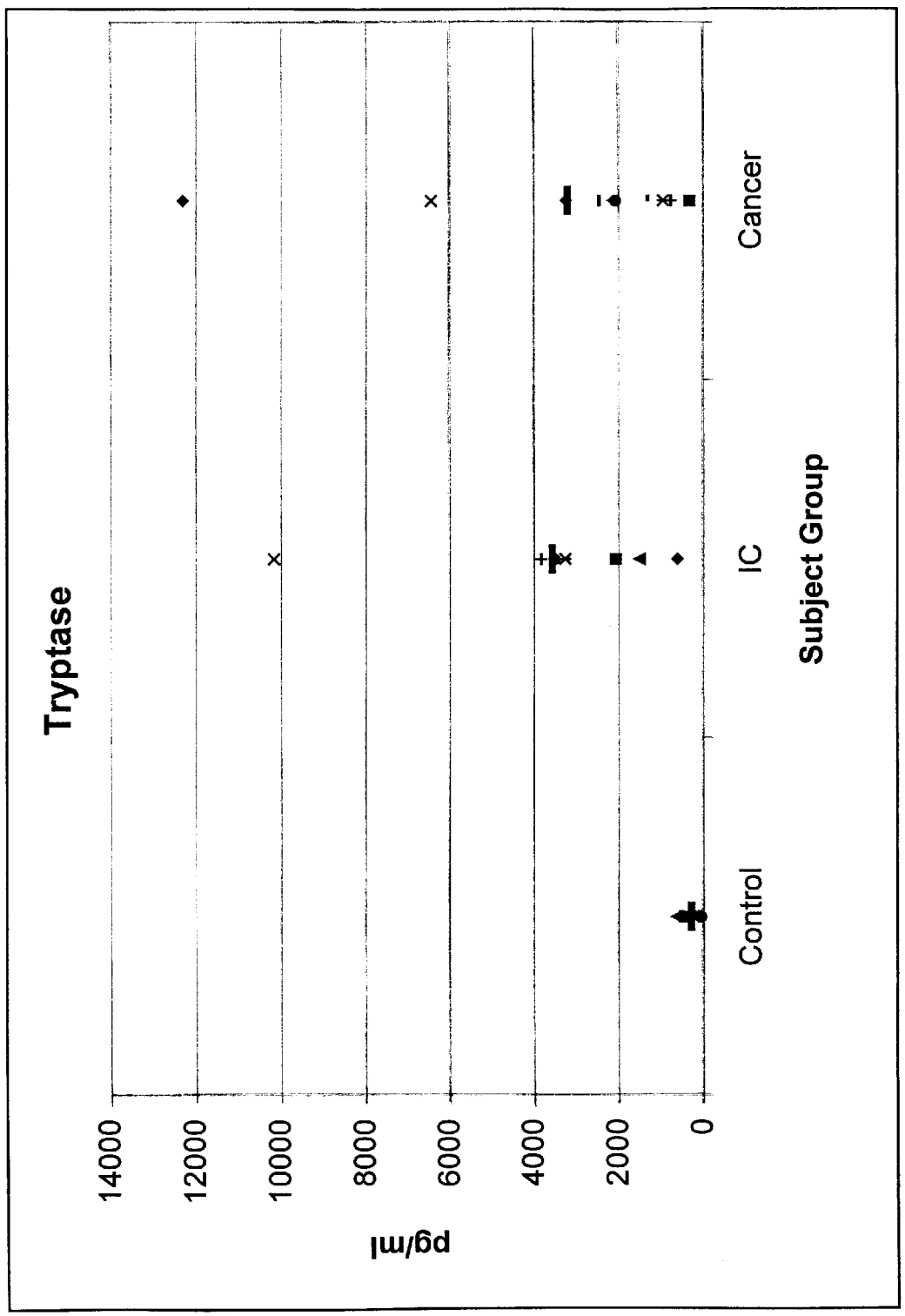
FIG. 5 is a graph depicting the concentration of tryptase in the urine of the same normal human control population, the population of human IC patients, and the population of human bladder cancer patients as depicted in FIG. 2. (See Example 4.)

The results are depicted in FIG. 5. Each patient within the individual control, IC, and bladder cancer groups is designated by a different symbol on the graph. Symbols have been duplicated in more than one patient groups; these duplicated symbols are unrelated.

In the same fashion as the previous Examples, the IC and Cancer patient groups displayed elevated levels of tryptase in their urine as compared to the Control patient group.

It is understood that the method disclosed above is not limited to the particular reagents and steps illustrated and described, but embraces all equivalent forms thereof which are encompassed by the following claims.

Bibiliography

Aldenborg, F., M. Fall and L. Enerback (1986), *Immunol.* 58:411–416.
Badalament, R. A., et al. (1987), *Cancer* 59(12):2078–2085.
Christmas, T. J. and J. Rode (1991), *Br. J. Urol.* 68:473–478.
Cohen, S. M., and Johansson (1992), *Urologic Clinics of North America* 19(3):421–428.
Dines, K. C. and H. C. Powell (1997), *J. Neuropath. Exp. Neurol.* 56:627–640.
Feltis, J. T., R. Perez-Marrero, and L. E. Emerson (1987), *J. Urol.* 138:4243.
Ghoniem, G. M. et al. (1993), *World J. Urol.* 11:178–182.
Gillespie, L. (1993), *Br. J. Urol.* 72:293–297.
Hano, P. M. (1989), *Emergency Med.* p. 149.
Hurst, R. E. et al. (1993), *J. Urol.* 149:31–35.
Kastrup, J. et al. (1983), *Br. J. Urol.* 55:495–500.
Larsen, S. et al. (1982), *Br. J. Urol.* 54:2833–286.
Leon, A. et al. (1994), *Proc. Nat. Acad. Sci. USA* 91:3739–3743.
Letourneau, R. et al. (1992), *Int. J. Tissue React.* 14:307–312.
Lindsay, R. M. (1995), *Nature* 373:289.
Lundeberg, T. et al. (1993), *Br. J. Urol.* 71:427–429.
Lynes, W. L. et al. (1987), *J. Urol.* 138:746–752.
Lynes, W. L. et al. (1990), *Am. J. Surg. Pathol.,* 14:969–976.
Maness et al. (1994) *Neurosci. Behav. Rev.* 18:143.
Mattila, J. et al. (1983), *Virchows Arch.* 398:347–355.
"Medical World News," Jun. 9, 1986, p. 125.
Messing, E. M. (1991), In *Campbell's Urology* (sixth edition), W. B. Saunders Co., Philadelphia, Pa., pp. 982–1005.
Moore, M. W. et al. (1996), *Nature* 382:76–79.
Nickel, C. J., L. Emerson, and J. Cornish (1993), *J. Urol.* 149:716–718.
Niles et al. (1995), "Mast Cell Secretagogues in Bladder Inflammation," 9th International Congress of Immunology, Promega Corporation.
Okragly, A. J. and M. Haak-Frendscho (1997), *Exptl. Neurol.* 145:1–5.
Parsons, C. L. and S. G. Mulholland (1987), *J. Urol.* 138:513–516.
Parsons, C. L. et al. (1993), *J. Urol.* 150:845–484.
Pichel, J. G. et al. (1996), *Nature* 382:73–76.
Promega Technical Bulletin Nos. 243 (revised April 1997), 226 (revised October 1996), 221 (revised November 1996), 540 (revised November 1994), 149 (revised October 1996), and 543 (revised April 1995): available to the public by contacting Promega Corporation, 2800 Woods Hollow Road, Madison, Wis., 53711-5399, USA.
Ratner, V., D. Slade and K. Whitmore (1992), *J. Woman's Health* 1:63.
Sanchez, M. P., (1996) *Nature* 382:70–73.
Sant, G. R. and E. M. Meares, Jr. (1988), *J. Urol.* 139:272A.
Sant, G. (1993), *J. Assoc. Acad. Minor Phys.* 4:89–92.
Sant, G. R. and Theoharides, T., (1994), "The Role of the Mast Cell in Interstitial Cystitis," *Urologic Clinics of North America,* 31:41–53.
Stone, A. R. et al. (1992), *J. Urol.* 148:1406–1408.
Vliagoftis, H. et al. (1992), *Int. Arch. Allergy Immunol.* 98:398–409.
Yun, S.K. et al. (1992), *J. Urol.* 148:1145–1148.

What is claimed is:

1. A method of diagnosing or monitoring bladder cancer in a mammal comprising determining concentration of a urine-soluble protein selected from the group consisting of neurotrophin-3, glial cell line-derived neurotrophic factor, tryptase, and combinations thereof in urine from the mammal and from a control population of mammals with no history of bladder cancer; and then comparing the concentrations from the mammal with corresponding concentrations from the control population, wherein elevated levels of neurotrophin-3, glial cell line-derived neurotrophic factor, or tryptase in the mammal as compared to the control population is indicative of bladder cancer in the mammal.

2. The method of claim 1, wherein the concentration of the urine-soluble protein is analyzed using an enzyme-linked immunosorbent assay.

3. The method of claim 2, wherein the concentration of neurotrophin-3 is analyzed.

4. The method of claim 2, wherein the concentration of glial cell line-derived neurotrophic factor is analyzed.

5. The method of claim 2, wherein the concentration of tryptase is analyzed.

6. The method of claim 2, wherein the concentration of neurotrophin-3, glial cell line-derived neurotrophic factor, or tryptase is analyzed using corresponding double antibody-sandwich enzyme-linked immunosorbent assays specific for neurotrophin-3, glial cell line-derived neurotrophic factor, or tryptase.

7. The method of claim 1, wherein the mammal is a human.

8. A non-invasive method of diagnosing or monitoring bladder cancer in a human subject comprising:
(a) securing a urine sample from the human subject and from a control population of humans with no history of bladder cancer; and then
(b) determining the presence and concentration in the urine sample from the human subject and from the control population of humans of a urine-soluble protein selected from the group consisting of neurotrophin-3, glial cell line-derived neurotrophic factor, tryptase, and combinations thereof; and then comparing the concentrations from the human subject with corresponding concentrations from the control population, wherein elevated levels of neurotrophin-3, glial cell line-derived neurotrophic factor, or tryptase in the human subject as compared to the control population is indicative of bladder cancer in the human subject.

9. The method of claim 8, wherein in step (b) the presence and concentration of the urine-soluble protein is determined using an enzyme-linked immunosorbent assay.

10. The method of claim 9, wherein in step (b) the presence and concentration of neurotrophin-3 is determined.

11. The method of claim 9, wherein in step (b) the presence and concentration of glial cell line-derived neurotrophic factor is determined.

12. The method of claim 9, wherein in step (b) the presence and concentration of tryptase is determined.

13. The method of claim 9, wherein in step (b) the presence and concentration of neurotrophin-3, glial cell line-derived neutrotrophic factor, or tryptase is determined using corresponding double antibody-sandwich enzyme-linked immunosorbent assays specific for neurrotrophin-3, glial cell line-derived neurotrophic factor, or tryptase.

14. A method of diagnosing or monitoring bladder cancer in a human subject comprising:
(a) securing a urine sample from the human subject and from a control population of humans with no history of bladder cancer; and then
(b) acidifying the urine samples from the human subject and from the control population to a pH of about 3.0 or less and then neutralizing the urine samples; and then
(c) determining concentration in the urine samples from the human subject and from the control population of a urine-soluble protein selected from the group consisting of neurotrophin-3, glial cell line-derived neurotrophic factor, tryptase, and combinations thereof using a corresponding double antibody-sandwich enzyme-linked immunosorbent assay specific for the urine-soluble protein being analyzed; and then comparing the concentrations from the human subject with corresponding concentrations from the control population, wherein elevated levels of neurotrophin-3, glial cell line-derived neurotrophic factor, or tryptase in the human subject as compared to the control population is indicative of bladder cancer in the human subject.

15. A method of diagnosing or monitoring interstitial cystitis in a mammal comprising determining concentration of a urine-soluble protein selected from the group consisting of neurotrophin-3, glial cell line-derived neurotrophic factor, and combinations thereof in urine from the mammal and from a control population of mammals with no history of interstitial cystitis; and then comparing the concentrations from the mammal with corresponding concentrations from the control population, wherein elevated levels of neurotrophin-3 or glial cell line-derived neurotrophic factor in the mammal as compared to the control population is indicative of interstitial cystitis in the mammal.

16. The method of claim 15, wherein the concentration of the urine-soluble protein is analyzed using an enzyme-linked immunosorbent assay.

17. The method of claim 16, wherein the concentration of neurotrophin-3 is analyzed.

18. The method of claim 16, wherein the concentration of glial cell line-derived neurotrophic factor is analyzed.

19. The method of claim 16, wherein the concentration of neurotrophin-3 and glial cell line-derived neurotrophic factor is analyzed.

20. A non-invasive method of diagnosing or monitoring interstitial cystitis in a human subject comprising:
(a) securing a urine sample from the human subject and from a control population of humans with no history of interstitial cystitis; and then
(b) determining the presence and concentration in the urine sample from the human subject and from the control population of humans of a urine-soluble protein selected from the group consisting of neurotrophin-3, glial cell line-derived neurotrophic factor, and combinations thereof; and then comparing the concentrations from the human subject with corresponding concentrations from the control population, wherein elevated levels of neurotrophin-3 or glial cell line-derived neurotrophic factor in the human subject as compared to the control population is indicative of interstitial cystitis or bladder cancer in the human subject.

21. The method of claim 20, wherein the concentration of the urine-soluble protein is analyzed using an enzyme-linked immunosorbent assay.

22. The method of claim 21, wherein the concentration of neurotrophin-3 is analyzed.

23. The method of claim 21, wherein the concentration of glial cell line-derived neurotrophic factor is analyzed.

24. The method of claim 21, wherein the concentration of neurotrophin-3 and glial cell line-derived neurotrophic factor is analyzed.

25. A method of diagnosing or monitoring interstitial cystitis in a human subject comprising:
(a) securing a urine sample from the human subject and from a control population of humans with no history of interstitial cystitis; and then
(b) acidifying the urine samples from the human subject and from the control population to a pH of about 3.0 or less and then neutralizing the urine samples; and then
(c) determining concentration in the urine samples from the human subject and from the control population of a urine-soluble protein selected from the group consisting of neurotrophin-3, glial cell line-derived neurotrophic factor, and combinations thereof using a corresponding double antibody-sandwich enzyme-linked immunosorbent assay specific for the urine-soluble protein being analyzed; and then comparing the concentrations from the human subject with corresponding concentrations from the control population, wherein elevated levels of neurotrophin-3 or glial cell line-derived neurotrophic factor in the human subject as compared to the control population is indicative of interstitial cystitis in the human subject.

* * * * *